(12) United States Patent
Semple et al.

(10) Patent No.: US 6,214,798 B1
(45) Date of Patent: Apr. 10, 2001

(54) GNRH ANTAGONISTS BEING MODIFIED IN POSITIONS 5 AND 6

(75) Inventors: Graeme Semple, Gothenburg (SE); Guangcheng Jiang, San Diego, CA (US)

(73) Assignee: Ferring BV, Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/402,698

(22) PCT Filed: Apr. 13, 1998

(86) PCT No.: PCT/US98/07438

§ 371 Date: Jan. 3, 2000

§ 102(e) Date: Jan. 3, 2000

(87) PCT Pub. No.: WO98/46634

PCT Pub. Date: Oct. 22, 1998

Related U.S. Application Data

(63) Continuation-in-part of application No. 08/837,042, filed on Apr. 11, 1997, now Pat. No. 5,925,730.

(51) Int. Cl.[7] .................................................. A61K 38/00
(52) U.S. Cl. ........................... 514/15; 514/800; 530/313; 530/328; 930/110
(58) Field of Search ................... 514/15, 800; 530/313, 530/328; 930/110

(56) References Cited

U.S. PATENT DOCUMENTS

| | | | |
|---|---|---|---|
| 4,508,921 | * 4/1985 | Amato et al. | 562/443 |
| 4,800,191 | 1/1989 | Schally et al. | 514/15 |
| 4,866,160 | 9/1989 | Coy | 530/313 |
| 4,935,491 | 6/1990 | Folkers et al. | 530/313 |
| 5,073,624 | 12/1991 | Coy et al. | 530/313 |
| 5,171,835 | 12/1992 | Janaky et al. | 530/313 |
| 5,198,533 | 3/1993 | Schally et al. | 530/313 |
| 5,296,468 | 3/1994 | Hoeger et al. | 514/15 |
| 5,470,947 | 11/1995 | Folkers et al. | 530/313 |
| 5,491,217 | 2/1996 | Haviv et al. | 530/313 |
| 5,506,207 | 4/1996 | Rivier et al. | 514/15 |
| 5,516,887 | 5/1996 | Deghenghi | 530/313 |
| 5,925,730 | * 7/1999 | Semple et al. | 530/328 |

FOREIGN PATENT DOCUMENTS

WO 9640757   12/1996   (WO).

OTHER PUBLICATIONS

Jiang et al., J. Med. Chem. (1997), 40, 3739–3748.*
Jiang, et al., Pept.: Chem., Struct. Biol. Proc. Am. Pept. Symp., 13th, Meeting Date 1993, 403–5, 1994.
Yanaihara et al., Biochem. Biophys. Res. Commun., 51(1), 165–73, 1973.
Rivier, et al., J. Med. Chem., 1995, 2649–2662, vol. 38.
Rivier, et al., J. Med. Chem., 1992, vol. 35, 4270–4278.

* cited by examiner

Primary Examiner—Dwayne C. Jones
Assistant Examiner—C. Delacroix-Muirheid
(74) Attorney, Agent, or Firm—Fitch, Even, Tabin & Flannery

(57) ABSTRACT

Peptides are provided which have improved duration of GnRH antagonistic properties. These antagonists may be used to regulate fertility and to treat steroid-dependent tumors and for other short-term and long-term treatment indications. These antagonists have a derivative of aminoPhe or its equivalent in the 5- or the 5- and 6-positions. This derivative is modified so as to contain a carbamoyl group or heterocycle, including a urea moiety, in its side chain. Decapeptides having the formula:

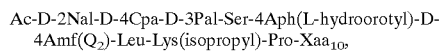

Ac-D-2Nal-D-4Cpa-D-3Pal-Ser-4Aph(L-hydroorotyl)-D-4Amf($Q_2$)-Leu-Lys(isopropyl)-Pro-$Xaa_{10}$, wherein $Q_2$ is Cbm or MeCbm and $Xaa_{10}$ is D-Ala-ol or Ala-ol are particularly effective and continue to exhibit very substantial suppression of LH secretion at 96 hours following injection.

20 Claims, No Drawings

GNRH ANTAGONISTS BEING MODIFIED IN POSITIONS 5 AND 6

This application is a continuation-in-part of our earlier application Ser. No. 08/837,042, filed Apr. 11, 1997, and now U.S. Pat. No. 5,925,730.

This invention relates generally to peptides which are antagonists of human gonadotropin releasing hormone (GnRH) and which have advantageous physical, chemical and biological properties. More particularly, the present invention relates to decapeptides which inhibit gonadal function and the release of the steroidal hormones progesterone and testosterone for periods of longer duration, and to methods of administering pharmaceutical compositions containing such decapeptides for such purpose and particularly to manage conditions resulting from the hypersecretion of gonadal steroids.

BACKGROUND OF THE INVENTION

Follicle stimulating hormone (FSH) and luteinizing hormone (LH), sometimes referred to as gonadotropins or gonadotropic hormones, are released by the pituitary gland which is attached by a stalk to the hypothalamus.

Hormone release by the anterior lobe of the pituitary gland usually requires prior release of hormones produced by the hypothalamus, such as the GnRH decapeptide.

The administration of GnRH analogs that are antagonistic to the normal function of GnRH has been used to suppress secretion of gonadotropins generally in mammals and to suppress or delay ovulation.

The search for improved GnRH antagonists has resulted in the making of Antide, i.e. [Ac-D-2Nal$^1$, D-4ClPhe$^2$, D-3Pal$^3$, Lys(Nic)$^5$, D-Lys(Nic)$^6$, ILys$^8$, D-Ala$^{10}$]-GnRH; and Cetrorelix, i.e. [Ac-D-2Nal$^1$, D-4ClPhe$^2$, D-3Pal$^3$, D-Cit$^6$, D-Ala$^{10}$]-GnRH. U.S. Pat. No. 5,516,887 describes GnRH antagonists which are said to be more effective than Antide in suppressing plasma testosterone, e.g.[Ac-D-2Nal$^1$, D-4ClPhe$^2$, D-3Pal$^3$, D-N$^\epsilon$-carbamoyl Lys$^6$, Ilys$^8$, D-Ala$^{10}$]-GnRH, which is referred to as Antarelix.

U.S. Pat. No. 5,296,468, issued Mar. 22, 1994, discloses the design and synthesis of a number of GnRH antagonists wherein the side chains of selected residues are reacted to create cyanoguanidino moieties, some of which subsequently spontaneously convert to a desired heterocycle, e.g. a 3-amino-1,2,4-triazole(atz). Such cyanoguanidino moieties are built upon the omega-amino group in an amino acid side chain, such as lysine, ornithine, 4-amino phenylalanine (4Aph) or an extended chain version thereof, such as 4-amino homophenylalanine (4Ahp). GnRH antagonists having such significantly modified or unnatural amino acids in the 5- and 6-positions exhibit good biological potency, and those built upon Aph are generally considered to be preferred. One that is especially preferred is Azaline B, i.e. [Ac-D-2Nal$^1$, D-4ClPhe$^2$, D-3Pal$^3$, 4Aph(atz)$^5$, D-4Aph (atz)$^6$, ILys$^8$, D-Ala$^{10}$]-GnRH. U.S. Pat. No. 5,506,207 discloses biopotent GnRH antagonists wherein aminosubstituted phenylalanine side chains of residues in the 5- and 6-positions are acylated; one particularly potent decapeptide is Acyline, i.e. [Ac-D-2 Nal$^1$, D-4CiPhe$^2$, D-3Pal$^3$, 4Aph(Ac)$^5$, D-4Aph(Ac)$^6$, ILys$^8$, D-Ala$^{10}$]-GnRH.

Despite the attractive properties of this group of GnRH antagonists, the search has continued for still further improved GnRH antagonists, particularly those which exhibit long duration of biological action. It can frequently be important that a peptide analog should exhibit a long duration of activity with respect to LH secretion, a property which may be enhanced by the peptide's resistance to proteolytic enzyme degradation in the body for both short-term and long-term treatment indications. In addition, to facilitate administration of these compounds to mammals, particularly humans, without significant gelling, it is considered extremely advantageous for such GnRH antagonistic decapeptides to have high solubility in water at normal physiologic pH, i.e. about pH 5 to about pH 7.4.

SUMMARY OF THE INVENTION

It has now been found that certain other modifications to the 5-position residue, or to the 5- and 6-position residues, in this subclass of GnRH antagonists, which includes Cetrorelix, Antarelix, Acyline, Antide and others, unexpectedly result in compounds which when administered sc exhibit the particularly advantageous property of long duration of bioactivity. These modifications are made to a residue of 4aminoPhe or its equivalent 4Aph or to 4-aminomethyl phenylalanine (4Amf) wherein the primary amino group is bonded to a methyl group attached in the 4- or para-position. In such modifications, the amino group of the side chain is reacted with an isocyanate to form a urea group or reacted with a heterocyclic carboxylic acid containing at least 2 nitrogen atoms arranged to constitute a urea moiety. The preferred heterocyclic reactants are D- or L-hydroorotic acid (Hor) (C$_4$N$_2$H$_5$(O)$_2$COOH) and D- or L-2-Imidazolidone-4-carboxylic acid (Imz) (C$_3$N$_2$H$_5$(O)COOH).

Generally, GnRH antagonist decapeptides having the following formula, and closely related analogs and the pharmaceutically acceptable salts, are found to have improved pharmacological properties, particularly long duration of bioactivity:

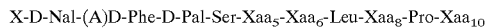

wherein:

X is an acyl group having up to 7 carbon atoms or Q, with Q being

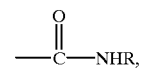

and with R being H or lower alkyl;

A is 4Cl, 4F, 4Br, 4NO$_2$, 4CH$_3$, 4OCH$_3$, 3,4Cl$_2$ or C$^\alpha$Me4Cl;

Xaa$_5$ is Aph(Q$_1$) or Amf(Q$_1$) with Q$_1$ being

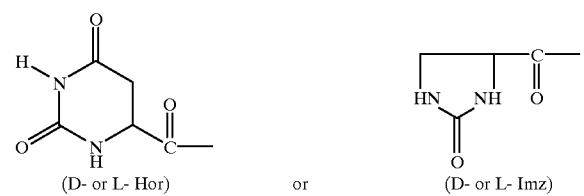

Xaa$_6$, is D-Aph(Q$_2$)D-Amf(Q$_2$), D-Lys(Nic), D-Cit, D-Hci or D-Pal, with Q$_2$ being For, Ac, 3-amino-1,2,4 triazole, Q or Q$_1$;

Xaa$_8$ is Lys(ipr), Arg, Har, Arg(Et$_2$) or Har(Et$_2$); and

Xaa$_{10}$ is D-Ala-NH$_2$, D-Ala-ol, Ala-ol, NHCH$_2$CH$_3$, Gly-NH$_2$, AzaGly-NH$_2$, Ala-NH$_2$, Agl-NH$_2$, D-Agl-NH$_2$, Agl(Me)—NH$_2$ or D-Agl(Me)-NH$_2$, provided however that the α-amino group of Xaa$_5$ may optionally be methylated; and provided further that when Xaa$_6$ contains D- or L-Hor or D- or L-Imz, Xaa₅ may have Ac, For or 3-amino-1,2,4-triazole as $Q_1$, and that when Xaa₆ contains Q, Xaa₅ may also contain Q.

In another aspect, the invention provides a method for invivo or invitro diagnosis of a condition where GnRH is causing excess hormonal secretion or tumor growth, which method comprises administering a GnRH antagonist peptide of the type described above and monitoring for hormonal secretion or for tumor cell proliferation.

In still another aspect, the invention provides an intermediate for making a GnRH antagonist peptide having the formula:

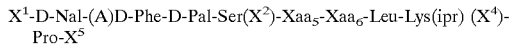

wherein:

$X^1$ is an α-amino-protecting group;

A is 4Cl or 4F;

$X^2$ is H or an hydroxyl-protecting group;

Xaa₅ is Aph($Q_1$) or Amf($Q_1$) with $Q_1$ being a D-isomer, an L-isomer or a D/L-isomer mixture of either

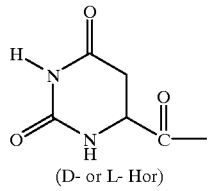 or 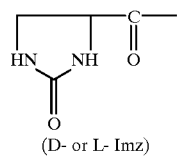

(D- or L- Hor)  (D- or L- Imz)

Xaa₆ is D-Aph($Q_2$), D-Amf($Q_2$) or D-Pal, with $Q_2$ being Ac, $Q_1$, carbamoyl or methylcarbamoyl;

$X^4$ is an acid-labile amino-protecting group; and $X^5$ is D-Ala-, Gly-, Ala-, Agl-, D-Agl-, Agl(Me)-, or D-Agl(Me)-resin support; N(Et)-resin support; an amide of D-Ala, Gly or Ala; ethylamide; AzaGly-NH₂; or OH, provided however that the α-amino group of Xaa₅ may optionally be methylated.

These antagonists are particularly useful to suppress the secretion of gonadotropins and as fertility regulators in humans because they exhibit long duration of activity, i.e. continuing to substantially suppress LH secretion for at least about 4 days. They have improved solubility in aqueous buffers at physiologic pHs and acceptable side effects with respect to stimulation of histamine release, i.e. better than the GnRH superagonists which are now being clinically used; they also exhibit minimal gelling upon subcutaneous (sc) injection at effective concentrations. These GnRH antagonists also perform well in an anaphylactoid assay causing a relatively small wheal. As a result, these peptides find particular use in administration to mammals, especially humans, as fertility regulators and for the treatment of pathological conditions such as precocious puberty, hormone-dependent neoplasia, dysmenorrhea, endometriosis, steroid-dependent tumors, and the other short-term and long-term indications mentioned hereinbefore. They are also useful diagnostically.

Because these GnRH antagonists are readily soluble in the physiologic pH range of about 5 to about 7.4, they can be formulated and administered in concentrated form, particularly at a pH between about 5 and about 7. Because of their polar character, they are particularly suitable for use in slow-release preparations based upon known copolymers. Because these GnRH antagonists exhibit effective suppression of LH and FSH for long duration, they are also particularly effective for the contraceptive treatment of male mammals (with the optional administration of testoterone) and for the treatment of steroid-dependent tumors.

DETAILED DESCRIPTION OF THE PREFERRED EMBODIMENTS

During the last 10 to 12 years, the particular properties of each of the 10 residues in the sequence of GnRH, from the standpoint of creating an effective antagonist, have been studied in depth, and as a result of these studies, it has been discovered that there are various equivalent residues that can be chosen and that substitutions of one of these equivalents for another does not significantly detract from the biological potency of decapeptide GnRH antagonists. Such equivalent substitutions may be made in the GnRH antagonists of the present invention.

For example, it has become generally accepted that the inclusion of a para-substituted D-Phe or 2,4 dichloro-substituted D-Phe or D-C$^α$Me4ClPhe or D-pentamethyl (Me₅)Phe residue in the 2-position adds significantly to GnRH antagonist activity; however, the specific identity of the ring substituent is of only relatively minor importance when selected from among the following: chloro, fluoro, bromo, nitro, methyl and alkoxy. Therefore, such residues in the 2-position are considered to be the equivalent of D-4ClPhe which is commonly used therein. Phe⁷ is considered to be equivalent to Leu⁷. The N-terminus is preferably N-acylated, preferably by acetyl (Ac), but also by other acyl groups having up to 7 carbon atoms, e.g. formyl (For), acrylyl (Acr), n-propionyl (Pn), butyryl (By), valeryl (Vl), vinylacetyl (Vac) and benzoyl (Bz); alternatively, it may be modified by a substituted or unsubstituted carbamoyl. Other longer acyl groups are considered to be equivalents but are less preferred. The α-amino group on the 5-position residue may be optionally methylated, as disclosed in U.S. Pat. No. 5,110,904, to increase solubility in water, but such modification may result in a shortening of duration of LH suppression and in greater potential for histamine release. The C-terminus is preferably D-Ala-NH₂, D-Ala-ol or Ala-ol; however, Gly-NH₂, NHCH₂CH₃, AzaGly-NH₂, Ala-NH₂, Agl-NH₂, D-Agl-NH₂, Agl(Me)-NH₂ and D-Agl(Me)-NH₂ may instead be used as they are considered to be known equivalents.

As stated hereinbefore, the present invention is considered to provide a family of GnRH antagonists represented by the following formula:

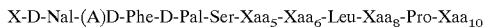

and the pharmaceutically acceptable salts thereof wherein:

X is For, Ac, Acr, Pn, By, Vl, Vac, Bz or Q, with Q being

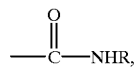

and with R being H or lower alkyl;

A is 4Cl, 4F, 4Br, 4NO₂, 4CH₃, 4OCH₃, 3,4Cl₂ or C$^α$Me4Cl;

Xaa$_5$ is Aph(Q$_1$) or Amf(Q$_1$) with Q$_1$ being

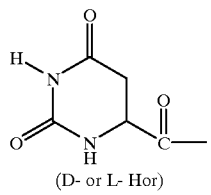  or  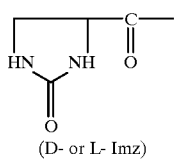

(D- or L- Hor)  or  (D- or L- Imz)

Xaa$_6$ is D-Aph(Q$_2$), D-Amf(Q$_2$), D-Lys(Nic), D-Cit:, D-Hci or D-Pal, with Q$_2$ being For, Ac, 3-amino-1,2,4 triazole, Q or Q$_1$;

Xaa$_5$ is Lys(ipr), Arg, Har, Arg(Et$_2$) or Har(Et$_2$); and Xaa$_{10}$ is D-Ala-NH$_2$, D-Ala-ol, Ala-ol, NHCH$_2$CH$_3$, Gly-NH$_2$, AzaGly-NH$_2$, Ala-NH$_2$, Agl-NH$_2$, D-Agl-NH$_2$, Agl(Me)-NH$_2$ or D-Agl(Me)-NH$_2$, provided however that the α-amino group of Xaa$_5$ may optionally be methylated.

In a closely related family of GnRH antagonists, Xaa$_5$ may have either Ac, For or 3-amino-1,2,4-triazole as Q$_1$, in which case Xaa$_6$ includes Q$_2$ in the form of D- or L--Hor or D-or L-Imz.

In another closely-related family of GnRH antagonists wherein Xaa$_6$ includes Q, Xaa$_5$ also includes Q.

By D-Nal is meant the D-isomer of alanine which is substituted by naphthyl on the β-carbon atom, i.e., also referred to as β-D-Nal or 3-D-Nal. Preferably D-2Nal is employed wherein the attachment to naphthalene is at the 2-position on the ring structure; however, D-1Nal may also be used. D-Cpa represents chloro-D-Phe, and D-4ClPhe, i.e. D-4Cpa, is preferred. D-Pal represents the D-isomer of alanine which has been substituted by pyridyl on the β-carbon atom; preferably, the linkage is to the 3-position on the pyridine ring, i.e. D-3Pal (β-3-pyridyl-D-Ala), although D-2Pal(β-2-pyridyl-D-Ala) might instead be used. By 4Aph is meant 4NH$_2$Phe wherein the amino substituent on the phenyl ring is at the 4-position; 3NH$_2$Phe(3Aph) is considered to be its equivalent in these analogs. Moreover, it is believed that 2NH$_2$Phe is also equivalent from the standpoint of biopotency. By 4Amf is reant 4NH$_2$CH2Phe where there is a methylene linkage to the side chain amino group; 3NH$_2$CH$_2$Phe(3Amf) is considered equivalent. By Hor or L-Hor is meant L-hydroorotyl, and by Imz or L-Imz is meant L-2-imidazolidone-4-carbonyl—either of which may also be used as the D-isomer or the D/L mixture. By atz is meant 3-amino-1,2,4-triazole. Aph(atz) is also known by the more precise chemical name 4-(3'-amino-1H-1',2',4'-triazoyl-5'-yl) aminophenylalanine. By Lys(Nic) is meant N$^ε$-nicotinoyl lysine, i.e. the ε-amino group of Lys is acylated with 3-carboxypyridine. By D-Cit is meant the D-isomer of citrulline, and by D-Hci is meant the D-isomer of homocitrulline, which is also D-N$^ε$-carbamoyl lysine. By ILys or Lys(ipr) is meant N$^ε$-isopropyl lysine where the ε-amino group of Lys is alkylated. By Ala-ol is meant alaninol, i.e. CH$_3$CH(NH$_2$)CH$_2$OH, and by AzaGly-NH$_2$ is meant NHNHCONH$_2$. By Har is meant homoarginine. By Agl is meant α-aminoglycine. By Cbm is meant carbamoyl, and by MeCbm is meant methylcarbamoyl or —CONHCH$_3$. By lower alkyl is meant C$_1$ to C$_5$, preferably C$_1$ to C$_3$, and more preferably C$_1$ or C$_2$, i.e. methyl(Me) or ethyl(Et).

Although the preferred D-isomers for incorporation in the 6-position of these GnRH antagonists are specifically disclosed, it should be understood that as a result of the extensive research in the field over the past two decades, there are many known equivalent D-isomers. Such prior art D-isomer substitutions may be compatible and not detract from the biopotency afforded by the specific 5-position substitutions disclosed herein, and may optionally be utilized.

A preferred subgenus of GnRH antagonists has the formula:

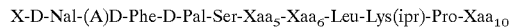

and the pharmaceutically acceptable salts thereof wherein:

X is For, Ac, Acr, Pn, By, Vl, Vac, Bz or Q, with Q being

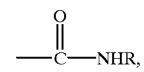

and with R being H or lower alkyl,

A is 4Cl or 4F;

Xaa$_5$ is Aph(Q$_1$) or Amf(Q$_1$) with Q$_1$ being

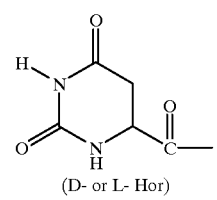  or  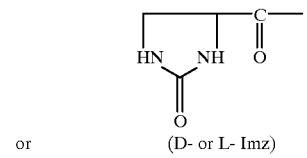

(D- or L- Hor)  or  (D- or L- Imz)

Xaa$_6$ is D-Aph(Q$_2$), D-Amf(Q$_2$), D-Cit, D-Lys(Nic) or D-Pal, with Q$_2$ being For, Ac, Q or Q$_1$; and Xaa$_{10}$, is D-Ala-NH$_2$, D-Ala-ol, Ala-ol, NHCH$_2$CH$_3$ or Gly-NH$_2$.

An additional preferred subgenus of GnRH antagonists has the formula:

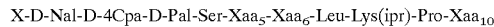

and the pharmaceutically acceptable salts thereof wherein:

X is Ac or Q, with Q being

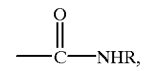

and with R being H or methyl;

Xaa$_5$ is Aph(Q$_1$) or Amf(Q$_1$) with Q$_1$ being

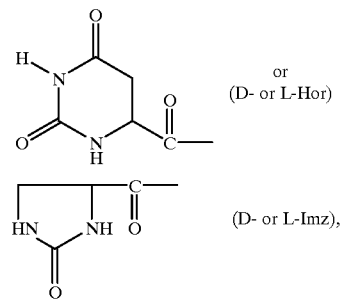

Xaa$_6$ is D-Aph(Q$_2$), D-Amf(Q$_2$) or D-Pal, with Q$_2$ being Ac, Q or Q$_1$; and Xaa$_{10}$ is D-Ala-NH$_2$, D-Ala-ol or Ala-ol.

Another preferred subgenus of GnRH antagonists has the formula:

MeCbm-D-2Nal-D-4Cpa-D-3Pal-Ser-4Aph(Hor)-D-Xaa$_6$-Leu-ILys-Pro-Xaa$_{10}$ and the pharmaceutically acceptable salts thereof wherein
D-Xaa$_6$ is D-4Amf(Q$_1$), D-4Aph(Q$_1$) or D-3Pal, with Q$_1$ being D-Hor or

and with R being H or lower alkyl, and preferably H or methyl; and wherein
Xaa$_{10}$ is D-Ala-NH$_2$, D-Ala-ol or Ala-ol.

The compounds of the present invention can be synthesized by classical peptide solution synthesis, and such synthesis is preferred for large quantities of product. To obtain limited quantities, e.g. less than 1 kg, it may be preferable to synthesize them using a solid phase technique. Side-chain protecting groups, as are well known in the art, are preferably included as a part of any amino acid which has a particularly reactive or labile side chain when it is being coupled into the chain being built upon the resin. Such synthesis provides a fully protected intermediate peptidoresin, such as X$^1$-D-Nal-(A)D-Phe-D-Pal-Ser (X$^2$)-Xaa$_5$-Xaa$_6$-Leu-Lys(ipr) (X$^4$)-Pro-X$^5$.

One example of a chemical intermediate, which might be used to synthesize a GnRH antagonist having a desired residue in the 5- and 6-positions containing hydroorotyl or the like is represented by the formula: X$^1$-D-Nal-D-4Cpa-D-Pal-Ser(X$^2$)-Aph(X$^3$)-D-Aph(X$^3$)-Leu-ILys(X$^4$)-Pro-X$^5$. In synthesizing peptide intermediates having this formula and other analogs, groups X$^1$ to X$^5$ as set forth hereinafter may be employed.

X$^1$ is an α-amino protecting group of the type known to be useful in the art in the stepwise synthesis of polypeptides and when X in the desired peptide composition is a particular acyl group, that group may be used as the protecting group. Among the classes of α-amino protecting groups covered by X$^1$ are (1) acyl-type protecting groups, such as formyl(For), trifluoroacetyl, phthaloyl, p-toluenesulfonyl (Tos), benzoyl(Bz), benzenesulfonyl, dithiasuccinoyl(Dts) o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl(Z), fluorenylmethyloxycarbonyl(Fmoc) and substituted benzyloxycarbonyl, such as p-chlorobenzyloxy-carbonyl (ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred α-amino protecting group is Boc.

X$^2$ is a protecting group for the hydroxyl side chain of Ser, e.g. Ac, Bz, trityl, 2,6-dichlorobenzyl (DCB) or benzyl ether(Bzl) and is preferably Bzl.

X$^3$ is a protecting group for a side chain amino group which is not removed when the α-amino protecting group or another amino-protecting group is removed. Illustrative examples include (1) base-labile groups, such as Fmoc, or some other weak-acid stable, aromatic urethane-type protecting group; (2) thiol-labile groups, such as dithiasuccinoyl(Dts) which may be removed or cleaved by thiolysis; (3) hydrazine-labile groups, such as phthaloyl(Pht) which is cleaved by hydrazinolysis; (4) nucleophile-labile groups, such as o-nitrophenylsulfenyl(Nps) and the like which are cleaved by thioacetamide or by weak acids or their salts; (5) photolabile groups which are cleaved by photolysis; and (6) groups selectively removable by reduction, such as Dts. Fmoc is preferred for a Boc SPPS strategy.

X$^4$ is an acid-labile protecting group for a primary or secondary amino side chain group, such as Z or 2ClZ.

X$^5$ may be D-Ala-, Gly-, Ala-, Agl-, D-Agl-, Agl(Me)- or D-Agl(Me)-NH-[resin support], or N(Et)-[resin support]; X$^5$ may also be an amide either of Gly or Ala or D-Ala, a lower alkyl-substituted amide attached directly to Pro, AzaGly-NH$_2$, or -OH (free acid). When X$_5$ is free acid, the intermediate is a nonapeptide fragment which is designed to be coupled to D- or L-alaninol to provide a decapeptide having an alcohol at the C-terminus.

The criterion for selecting side chain protecting groups x$^2$ through X$^4$ is that the protecting group should generally be stable to the reagent under the reaction conditions selected for removing the α-amino protecting group (preferably Boc) at each step of the synthesis. These protecting groups generally should not be split off under coupling conditions but should be removable upon completion of the synthesis of the desired amino acid sequence under reaction conditions that will not alter the peptide chain. The protecting groups initially employed for the 5- and 6-position residues are preferably removed and selective reactions are carried out prior to cleavage of the ultimate peptide from the resin, as explained hereinafter. If a decapeptide intermediate is synthesized as set forth hereinbefore, the X$^3$ protecting groups may be desirably individually removable.

When the X$^5$ group is D-Ala-NH-[resin support], an amide bond connects D-Ala to a BHA resin or to a MBHA resin; this is likewise the case when Agl or D-Agl is used at the C-terminus. When X$^5$ is N(Et)-[resin support], an ethylamide bond connects Pro to an N-alkylaminomethyl resin (NAAM).

When the N-terminus is to be acetylated, for example, it is possible to employ acetyl as the X$^1$ protecting group for the α-amino group of β-D-Nal in the 1-position by adding it to the amino acid before it is coupled to the peptide chain; however, a reaction is preferably carried out with the peptide intermediate on the resin. After deblocking the α-amino group and while desired side chain groups remain protected, acetylation is preferably carried out by reacting with acetic anhydride, alternatively reaction can be carried out with acetic acid, in the presence of diisopropyl or dicyclohexyl carbodiimide (DIC or DCC), or by some other suitable acylation reaction as known in the art. A similar procedure is carried out when a carbamoyl or substituted carbamoyl group is desired at the N-terminus. When the deprotected side chain amino groups are modified while the residue is part of the peptide chain, the reaction may be carried out using an appropriate isocyanate in the presence of an appropriate base, for example, N,N-diisopropylethylamine (DIEA), although the use of such a base is optional. When an unsubstituted carbamoyl group is desired in the final product, the deprotected amino side chain may be reacted with benzyl isocyanate, p-tosyl isocyanate, trimethylsilyl isocyanate or tert-butyl isocyanate, with the latter being preferred. Using such a strategy, the t-butyl moiety is removed during cleavage from the resin, leaving the carbamoyl group.

The invention also provides a novel method for making such a GnRH antagonist having, for example, the formula: Ac-D-2Nal-D-4Cpa-D-3Pal-Ser-4Aph(Hor)-D-4Aph(Ac)-Leu-ILys-Pro-D-Ala-NH$_2$, which method comprises (a) forming an intermediate peptide having the formula: Boc-D-4Aph($X^3$)-Leu-ILys ($X^4$)-Pro-$X^5$ wherein $X^3$ is a base-labile, hydrazinelabile or other appropriately labile protecting group for an amino group; $X^4$ is an acid-labile protecting group for an amino side chain; and $X^5$ is D-Ala-NH-[resin support]; (b) removing $X^3$ from D-4Aph to deprotect the side chain primary amino group of this amino acid residue of the intermediate peptide; (c) reacting this deprotected side chain primary amino group with acetic anhydride; (d) completing the chain elongation to create the intermediate $X^1$-D-2Nal-D-4Cpa-D-3Pal-Ser($X^2$)-4Aph($X^3$)-D-4Aph(Ac)-Leu-Ilys($X^4$)-Pro-$X^5$, wherein $X^1$ is hydrogen or an α-amino protecting group and $X^2$ is hydrogen or a protecting group for a hydroxyl group of Ser; (e) deblocking the α-amino group at the N-terminus and acetylating; (f) removing $X^3$ from 4Aph and reacting the deprotected primary amino group with hydroorotic acid; and (g) splitting off any remaining protecting groups and/or cleaving from resin support included in $X^5$.

Final purification of the peptide is effected by chromatography and preferably by using RP-HPLC, as known in the art, see J. Rivier, et al. *J. Chromatography*, 288, 303–328 (1984), and C. Miller and J. Rivier, *Biopolymers* (Peptide Science), 40, 265–317 (1996).

The GnRH antagonists of the invention are considered to be effective at levels of less than 100 micrograms per kilogram of body weight, when administered subcutaneously at about noon on the day of proestrus, to prevent ovulation in female rats. For prolonged suppression of ovulation, it may be necessary to use dosage levels in the range of from about 0.1 to about 2.5 milligrams per kilogram of body weight. The antagonists are also effective to arrest spermatogenesis when administered to male mammals on a regular basis and can thus be used as contraceptives. Because these compounds will reduce testosterone levels and thus libido (an undesired consequence in the normal, sexually active male), it may be desirable to administer replacement dosages of testosterone along with the GnRH antagonist in order to achieve azoospermia while maintaining libido. These antagonists can also be used to regulate the production of gonadotropins and sex steroids and for other of the long-term and short-term indications as indicated hereinbefore, and they can be used in veterinary applications as contraceptives for pets.

The peptides provided by the invention are particularly soluble at physiological pHs and can be prepared as relatively concentrated solutions for administration, particularly for subcutaneous injection. These peptides are well-tolerated in the body and do not tend to gel when administered subcutaneously at effective concentrations. Generally pharmaceutical compositions including such peptides and a suitable pharmaceutically acceptable excipient can be administered iv, ip, subcutaneously or the like at levels of between about 0.001 mg to about 2.5 mgs per Kg of body weight per day, with 0.5 mg/kg/day usually being sufficient.

The appropriately protected D- or L-hydroorotyl-containing, carbamoyl-containing and/or D- or L-imidazolidone-carbonyl-containing amino acids may be synthesized and then employed in a chain elongation peptide synthesis. However, an equally valid synthesis is effected by initially incorporating an appropriately protected Aph, D-Aph, Amf or D-Amf residue at the desired position in the peptide intermediate, and this may be the laboratory method of choice where only small quantities are initially desired. This latter strategy is accomplished by subsequently deprotecting the particular residue (either immediately or subsequently during the synthesis) and then reacting the deprotected side chain amino group with the desired reagent.

The present invention is further described by the examples which follow.

EXAMPLE 1

The peptide having the formula: Ac-D-2Nal-D-4Cpa-D-3Pal-Ser-Lys(Nic)-D-Lys(Nic)-Leu-ILys-Pro-D-Ala-NH$_2$ (Antide) has been found to exhibit very good biological properties as a GnRH antagonist, as has the peptide which is presently referred to as Acyline and which differs from Antide in only the 5- and 6-positions. It has now been found that by using these molecules as a starting point and by making other substitutions in the 5- and 6-positions or in the 5-position of the decapeptide Acyline, GnRH antagonists having improved duration of bioactivity in vivo are obtained. With respect to positions 1–4 and 7–10, it is noted that Antide, Acyline and Azaline are all exactly the same.

The following decapeptide [4Aph(Hor)$^5$, D-4Aph(Cbm)$^6$]-Antide or [Ac-D-2Nal$^1$, D-4Cpa$^2$, D-3Pal$^3$, 4Aph(Hor)$^5$, D-4Aph(Cbm)$^6$, ILys$^8$, D-Ala$^{10}$]-GnRH is synthesized by solid-phase synthesis. This peptide has the following formula:

Ac-D-2Nal-D-4Cpa-D-3Pal-Ser-4Aph(L-hydroorotyl)-D-4Aph(carbamoyl)-Leu-Lys(isopropyl)-Pro-D-Ala-NH$_2$.

About 0.50 gram (0.54 mmol/g) of MBHA resin (Bachem) are initially used, and Boc-protected D-Ala is coupled to the resin over about a 2-hour period in dimethylformamide(DMF)/CH$_2$Cl$_2$ using about 0.65 millimole of Boc derivative and diisopropylcarbodiimide(DIC) and anhydrous 1-hydroxybenzotriazole (HOBt) as activating or coupling reagents. The D-Ala residue attaches to the MBHA residue by an amide bond.

Following the coupling of each amino acid residue, washing, deblocking and then coupling of the next amino acid residue are carried out in accordance with the following manual synthesis schedule for about 0.5 to 1 gram of starting resin:

| STEP | REAGENTS AND OPERATIONS | MIX TIMES MIN. |
|---|---|---|
| 1 | Methanol (MeOH) wash-15 ml. (2 times) | 1 |
| 2 | CH$_2$Cl$_2$ (DCM) wash-30 ml. (3 times) | 1 |
| 3 | 50% TFA plus 1% m-cresol in DCM-25 ml. (2 times) | 5, 20 |
| 4 | Isopropyl alcohol wash-20 ml. (2 times) | 1 |
| 5 | Triethylamine 10% in DCM-20 ml. (2 times). | 2 |
| 6 | MeOH wash-15 ml. (2 times) | 1 |
| 7 | DCM wash-20 ml. (3 times) | 1 |
| 8 | Boc-amino acid (0.5–1.0 mmole) and HOBt (0.5–1.0 mmole) in 10–20 ml. of dimethylformamide (DMF) :DCM or N-methylpyrrolidone (NMP) :DCM, depending upon the solubility of the particular protected amino acid, plus DIC or DCC (0.5–1.0 mmole) in DCM | 1–17 hours |
| 9 | MeOH wash-15 ml. (2 times) | 1 |
| 10 | DCM wash-20 ml. (3 times) | 1 |

The above schedule is used for coupling of each of the amino acids of the peptide of the invention after the first amino acid has been attached. N$^\alpha$Boc protection is used for each of the amino acids coupled throughout the synthesis. $N^\alpha$Boc-β-D-2Nal is prepared by a method known in the art, e.g. as described in detail in U.S. Pat. No. 4,234,571; it is also commercially available from SyntheTech, Oregon, U.S.A. The side chain primary amino groups of 4Aph in the 5-position and of D-4Aph in the 6-position are protected by Fmoc. Benzyl ether (Bzl) is preferably used as a side chain protecting group for the hydroxyl group of Ser; however, Ser may be coupled without side chain protection. $N^\alpha$Boc-Lys (ipr,Z) is used for the 8-position residue.

After adding D-4Aph for the 6-position residue as $N^{\alpha Boc}$-D-4Aph(Fmoc), the following intermediate is present: Boc-D-4Aph(Fmoc)-Leu-Lys(ipr,Z)-Pro-D-Ala-NH-[MBHA resin supports]. The side chain amino group on the 6-position residue is then modified after first removing the side-chain protection. The Fmoc protecting group is removed by successive treatments with 25 percent piperidine in DMF(10 ml) for about 15 minutes each. After washing the peptidoresin with DMF, the newly freed amino group is treated with a 20-fold excess of tert-butyl isocyanate in DMF at room temperature for about 12 hours, or until complete as checked using a ninhydrin test. The peptidoresin is then subjected to the standard wash, and Boc is removed in order to add the next residue.

The 5-position residue is then added as $N^\alpha$Boc-4Aph (Fmoc). Its side chain is then deprotected as before, and a reaction is carried out with 0.10 g (0.66 mmol) of L-hydroorotic acid, 90 mg (0.66 mmol) of HOBt and 0.66 mmol of DIC in 3 ml of DMF at room temperature for about 8 hours, or until complete as checked using a standard ninhydrin test. After washing and $N^\alpha$Boc removal, the synthesis of the decapeptide is completed by sequentially reacting with $N^\alpha$Boc-Ser(Bzl), $N^\alpha$Boc-D-3Pal, $N^\alpha$Boc-4Cpa, and $N^\alpha$Boc-D-2Nal.

After deblocking the α-amino group at the N-terminus using trifluoroacetic acid (TFA), acetylation is achieved using a large excess of acetic anhydride in dichloromethane (DCM) for about 30 minutes. Alternatively, the Fmoc protection of 4Aph is not removed until after the acetylation of the N-terminus, and the reaction with L-hydroorotic acid is then carried out.

The peptidoresin is dried, and following addition of anisole (0.5 ml.) as a scavenger, cleavage of the peptide from the resin and deprotection of the Ser and the Lys side chains are carried out at about 0° C. with 15 ml of HF for about 1.5 hours, with the removal of any remaining t-butyl moiety. After the removal of HF under vacuum, the resin is washed twice with 100 ml. of ethyl ether. The cleaved peptide is extracted with 0.2% TFA in 25% $CH_3CN/H_2O$, repeating the process and using 100 ml. each time. The extracts are pooled and lyophilized, and they provide about 600 mg of a crude peptide powder.

Purification of the peptide is then effected by preparative reverse-phase high performance liquid chromatography (RP-HPLC), as known in the art and specifically set forth in J. Rivier, et al. *J. Chromatography*, 288, 303–328 (1984). The first preparative RP-HPLC separation uses a TEAP (triethylammonium phosphate) buffer system, and a final separation is carried out using a 0.1% TFA (trifluoroacetic acid) gradient, all as described in detail in the *J. Chromatography* article. The peptide (about 30 mg) (hereinafter referred to as Peptide No. 1) is judged to be substantially homogeneous using capillary zone electrophoresis (CZE), and the purity is estimated to be about 98%. Amino acid analysis of the purified peptide is consistent with the formula for the prepared structure. Molecular weight as determined by liquid secondary ion mass spectrometry (LSIMS) is measured as 1631.9 Da, which is consistent with the expected mass of 1631.8 Da for this peptide.

Hydrophilicity is tested by measuring retention time using RP-HPLC with a gradient of 40% Buffer B to 70% Buffer B over 30 minutes, with Buffer A being TEAP pH 7.0 and Buffer B being 70% $CH_3CN$ and 30% Buffer A. Peptide No. 1 is more hydrophilic than Acyline, eluting earlier than Acyline. Its solubility in aqueous buffers at a pH of from about 5 to about 7 and its resistance to in vivo gelling, along with a long-acting biopotency to suppress circulating LH levels as described hereinafter, render it particularly suitable for administration by subcutaneous injection compared to other compounds of generally comparable biological efficacy.

The peptide is assayed in vivo to determine its effectiveness to suppress the secretion of LH in rats.

Measurement of circulating LH levels in castrated male Sprague-Dawley rats treated subcutaneously with the peptide is carried out as reported in C. Rivier et al. *Biol. Reproduc.*, 1983. 29, 374–378. The peptides are first dissolved at a concentration of 1.0 or 10 mg/ml in bacteriostatic water and then further diluted in 0.04 M phosphate buffer containing 0.1% BSA. Subsequent dilutions are made in phosphate buffer. The peptides are injected sc into 5 rats, and blood samples (300 μl) are collected under metotane anesthesia. Sera (50 μl) are tested for LH levels in duplicate using reagents provided by the National Pituitary and Hormone Distribution Program of the NIDDK. Testing shows that a dosage of 50 μg of peptide per rat suppresses LH secretion to levels that are far less than 50% of control levels throughout the 96-hour period following injection. Moreover, the levels measured after 96 hours are about only 30% of the LH levels exhibited by rats similarly injected with a dose of 50 micrograms of Acyline. Peptide No. 1 is considered to be very long-acting. Examination of the rats shows that the peptide was very well tolerated, with no significant gelling at the point of injection being detectable.

Experience gained from the testing of a large number of GnRH antagonists shows that a peptide exhibiting such long-acting suppression of LH would, if assayed in vivo in mature female Sprague-Dawley rats, fully block ovulation at a dosage of 2.5 micrograms.

EXAMPLE 1A

The synthesis set forth in Example 1 is repeated, substituting $N^\alpha$Boc-D-4Amf(Fmoc) for $N^\alpha$Boc-D-4Aph(Fmoc). Following deprotection of the D-4Amf side chain, reaction with t-butyl isocyanate is carried out as before. Cleavage from the resin and deprotection, followed by purification, are carried out as described in Example 1. The peptide Ac-D-2Nal-D-4Cpa-D-3Pal-Ser-4Aph(L-hydroorotyl)-D-4Amf(carbamoyl)-Leu-Lys (isopropyl)-Pro-D-Ala-$NH_2$ is obtained in the RP-HPLC purification and judged to be substantially homogeneous, with its purity estimated to be greater than 99 percent. MS analysis shows a mass of 1645.9 Da which compares favorably to the expected mass of 1645.8 Da. From the HPLC results,it can be seen that this peptide is more hydrophilic than Acyline.

Assaying this peptide in the standard in vivo rat LH suppression test shows that, at a dosage of 50 micrograms, it is as effective as Acyline in suppressing LH levels at 1, 2 and 3 days. At 96 hours, the LH levels are only about 25% of those of the rats injected with Acyline. Peptide No. 1A is considered to be very long-acting.

EXAMPLE 1B

To form the analog [4Aph(Hor)$^5$]-Acyline, the synthesis set forth in Example 1 is repeated substituting acetic anhydride for t-butyl isocyanate for the reaction with the deprotected position-6 side-chain. Cleavage of the decapeptide from the resin and deprotection, followed by purification, are carried out as described in Example 1. The peptide Ac-D-2Nal-D-4Cpa-D-3Pal-Ser-4Aph(L-hydroorotyl)-D-4Aph(acetyl)-Leu-Lys(isopropyl)-Pro-D-Ala-NH$_2$ is obtained in the RP-HPLC purification. It is judged to be substantially homogeneous, and its purity is estimated to be greater than 99 percent. MS analysis shows a mass of 1630.6 Da, which is in agreement with the calculated mass of 1630.8 Da.

Assaying this peptide in the standard in vivo rat test as in Example 1, shows that, at a dosage of 50 micrograms, the peptide is bioactive and about as effective as Acyline at day 1 through day 4. It is considered to exhibit very long-acting duration for the suppression of LH.

EXAMPLE 1C

The synthesis set forth in Example 1B is repeated substituting D/L hydroorotic acid for L-hydroorotic acid to form isomeric decapeptides. Cleavage from the resin and deprotection, followed by purification, are carried out as described in Example 1. The peptide Ac-D-2Nal-D-4Cpa-D-3Pal-Ser-4Aph(D/L-hydroorotyl)-D-4Aph(acetyl)-Leu-Lys(isopropyl)-Pro-D-Ala-NH$_2$ is obtained in the RP-HPLC purification. It is judged to be a homogeneous mixture of two compounds without other impurities. MS analysis shows a mass of 1630.6 Da, which is in agreement with the calculated mass of 1630.8 Da.

Assaying this peptide in the standard in vivo rat test as in Example 1, shows that, at a dosage of 50 micrograms, the peptide is bioactive and about as effective as Acyline at day 1 through day 4. It is considered to exhibit long-acting duration for the suppression of LH.

EXAMPLE 1D

The synthesis set forth in Example 1B is repeated substituting D-hydroorotic acid for L-hydroorotic acid to form the isomeric decapeptide. Cleavage from the resin and deprotection, followed by purification, are carried out as described in Example 1. The peptide Ac-D-2Nal-D-4Cpa-D-3Pal-Ser-4Aph(D-hydroorotyl)-D-4Aph(acetyl)-Leu-Lys(isopropyl)-Pro-D-Ala-NH$_2$ is obtained in the RP-HPLC purification. It is judged to be substantially homogeneous, and its purity is estimated to be greater than 98 percent. MS analysis shows a mass of 1630.8 Da, which is in agreement with the calculated mass of 1630.8 Da.

Assaying this peptide in the standard in vivo rat test as in Example 1, shows that, at a dosage of 50 micrograms, the peptide exhibits long-acting duration of bioactivity for the suppression of LH, being about as effective as Acyline at day 1 through day 4.

EXAMPLE 1E

The synthesis set forth in Example 1B is repeated substituting N$^\alpha$Boc-D-4FPhe for N$^\alpha$Boc-D-4ClPhe to form the decapeptide [D-4FPhe$^2$, 4Aph(Hor)$^5$]-Acyline. Cleavage from the resin and deprotection, followed by purification, are carried out as described in Example 1. The peptide Ac-D-2Nal-D-4Fpa-D-3Pal-Ser-4Aph(L-hydroorotyl)-D-4Aph(acetyl)-Leu-Lys(isopropyl)-Pro-D-Ala-NH$_2$ is obtained in the RP-HPLC purification. It is judged to be substantially homogeneous, and its purity is estimated to be greater than 99 percent. MS analysis shows a mass of 1615.1 Da, which is in agreement with the calculated mass of 1614.8 Da.

Assaying this peptide in the standard invivo rat test as in Example 1, shows that, at a dosage of 50 micrograms, the peptide is bioactive and about as effective as Acyline at day 1 through day 4. It is considered to exhibit long-acting duration for the suppression of LH.

EXAMPLE 1F

The synthesis set forth in Example 1B is repeated substituting N$^\alpha$Boc-4Amf(Fmoc) for N$^\alpha$Boc-4Aph(Fmoc) to form the decapeptide [4Amf(Hor)$^5$]-Acyline. Cleavage from the resin and deprotection, followed by purification, are carried out as described in Example 1. The peptide Ac-D-2Nal-D-4Cpa-D-3Pal-Ser-4Amf(L-hydroorotyl)-D-4Aph(acetyl)-Leu-Lys(isopropyl)-Pro-D-Ala-NH$_2$ is obtained in the RP-HPLC purification. It is judged to be substantially homogeneous, and its purity is estimated to be greater than 98 percent. MS analysis shows a mass of 1644.7 Da, which is in agreement with the calculated mass of 1644.8 Da.

Assaying this peptide in the standard in vivo rat test as in Example 1, shows that, at a dosage of 50 micrograms, the peptide is bioactive and about as effective as Acyline at 1 day through four days. It is considered to exhibit long-acting duration for the suppression of LH.

EXAMPLE 1G

The synthesis set forth in Example 1 is repeated; however, instead of reacting the side chain amino of D-4Aph with t-butyl isocyanate, it and the 4Aph residue are simultaneously reacted with hydroorotic acid to form the decapeptide [4Aph(Hor$^5$), D-4Aph(Hor)$^6$]-Antide. Cleavage from the resin and deprotection, followed by purification, are carried out as described in Example 1. The peptide Ac-D-2Nal-D-4Cpa-D-3Pal-Ser-4Aph(L-hydroorotyl)-D-4Aph(L-hydroorotyl)-Leu-Lys(isopropyl)-Pro-D-Ala-NH$_2$ is obtained in the RP-HPLC purification. It is judged to be substantially homogeneous, and its purity is estimated to be greater than 99 percent. MS analysis shows a mass of 1728.4 Da, which is in agreement with the calculated mass of 1728.8 Da. The results of the RP-HPLC show that this peptide is more hydrophilic than Azaline B which is in turn more hydrophilic than Acyline.

Assaying this peptide in the standard in vivo rat test as in Example 1, shows that, at a dosage of 50 micrograms, the peptide is bioactive and about as effective as Acyline at day 1 through day 4. It is considered to exhibit long-acting duration for the suppression of LH.

This synthesis is repeated substituting N$^\alpha$Boc-D-4Amf(Fmoc) for N$^\alpha$Boc-D-4Aph(Fmoc) to create the decapeptide [4Aph(Hor)$^5$, D-Amf(Hor)$^6$]-Antide, which is generally as biopotent in the suppression of secretion of LH.

EXAMPLE 1H

The synthesis set forth in Example 1 is repeated; however, instead of reacting the side chain amino of D-4Aph with t-butyl isocyanate, it is reacted with D-hydroorotic acid to form the decapeptide [4Aph(Hor$^5$), D-4Aph(D-Hor)$^6$]-Antide. Cleavage from the resin and deprotection, followed by purification, are carried out as described in Example 1. The peptide Ac-D-2Nal-D-4Cpa-D-3Pal-Ser-4Aph(L-hydroorotyl)-D-4Aph(D-hydroorotyl)-Leu-Lys(isopropyl)-Pro-D-Ala-NH$_2$ is obtained in the RP-HPLC purification. It is judged to be substantially homogeneous, and its purity is estimated to be greater than 98 percent. MS analysis shows a mass of 1728.7 Da, which is in agreement with the calculated mass of 1728.8 Da. The results of the RP-HPLC show that this peptide is more hydrophilic than Azaline B which is in turn more hydrophilic than Acyline.

Assaying this peptide in the standard in vivo rat test as in Example 1, shows that, at a dosage of 50 micrograms, the peptide is bioactive and about as effective as Acyline at day 1 through day 3. It is substantially more effective than Acyline at 4 days and is considered to exhibit very long-acting duration for the suppression of LH.

EXAMPLE 1I

The synthesis of the decapeptide [MeCbm-D-2Nal$^1$, 4Aph(Hor)$^5$]-Acyline is carried out by generally proceeding as set forth in Example 1B; however, instead of immediately removing the Fmoc-protecting group after adding N$^\alpha$Boc-4Aph(Fmoc), the synthesis of the decapeptide on the resin is completed. Then, after deblocking the N-terminus, instead of reacting with acetic anhydride, a reaction is carried out with methyl isocyanate to form the methylcarbamoyl at the N-terminus. Then, the Fmoc is removed and the side chain amino of 4Aph is reacted with L-hydroorotic acid as in Example 1B. Cleavage from the resin and deprotection, followed by purification, are carried out as described in Example 1. The peptide methylcarbamoyl-D-2Nal-D-4Cpa-D-3Pal-Ser-4Aph(L-hydroorotyl)-D-4Aph(acetyl)-Leu-Lys(isopropyl)-Pro-D-Ala-NH$_2$ is obtained in the RP-HPLC purification. It is judged to be substantially homogeneous, and its purity is estimated to be about 99 percent. MS analysis shows a mass of 1645.7 Da, which is in agreement with the calculated mass of 1645.8 Da. The results of the RP-HPLC show that this peptide is more hydrophilic than Azaline B which is in turn more hydrophilic than Acyline.

Assaying this peptide in the standard in vivo rat test as in Example 1, shows that, at a dosage of 50 micrograms, the peptide is bioactive and about as effective as Acyline at day 1 through day 3 and more effective by nearly 50% after 96 hours. It is considered to exhibit very long-acting duration for the suppression of LH.

EXAMPLE 1J

The synthesis set forth in Example 1 is repeated substituting N$^\alpha$Boc-D-3Pal for N$^\alpha$Boc-D-4Aph(Fmoc) and omitting the subsequent reaction with t-BuNCO to form the decapeptide [4Aph(Hor)$^5$, D-3Pal$^6$]-Antide. Cleavage from the resin and deprotection, followed by purification, are carried out as described in Example 1. The peptide Acetyl-D-2Nal-D-4Cpa-D-3Pal-Ser-4Aph(L-hydroorotyl)-D-3Pal-Leu-Lys(isopropyl)-Pro-D-Ala-NH$_2$ is obtained in the RP-HPLC purification. It is judged to be substantially homogeneous, and its purity is estimated to be greater than 99 percent. MS analysis shows a mass of 1574.7 Da, which is in agreement with the calculated mass of 1574.7 Da.

Assaying this peptide in the standard in vivo rat test as in Example 1, shows that, at a dosage of 50 micrograms, the peptide is bioactive and about as effective as Acyline through three days; however, after 96 hours, it exhibits suppression of LH level to values about 35% of those of Acyline. It is considered to exhibit very long-acting duration for the suppression of LH.

EXAMPLE 1K

The synthesis set forth in Example 1G is repeated substituting t-butyl isocyanate for hydroorotic acid to form the decapeptide [4Aph(Cbm)$^5$,D-4Aph(Cbm)$^6$]-Antide. Cleavage from the resin and deprotection, followed by purification, are carried out as described in Example 1.

The peptide Ac-D-2Nal-D-4Cpa-D-3Pal-Ser-4Aph(carbamoyl)-D-4Aph(carbamoyl)-Leu-Lys(isopropyl)- Pro-D-Ala-NH$_2$ is obtained in the RP-HPLC purification. It is judged to be substantially homogeneous, and its purity is estimated to be greater than 99 percent. MS analysis shows a mass of 1534.9 Da, which is in agreement with the calculated mass of 1534.7 Da.

Assaying this peptide in the standard in vivo rat test as in Example 1, shows that, at a dosage of 50 micrograms, the peptide is bioactive and about as effective as Acyline through four days. It is considered to exhibit long-acting duration for the suppression of LH.

EXAMPLE 1L

The synthesis set forth in Example 1G is repeated substituting methyl isocyanate for hydroorotic acid to form the decapeptide [4Aph(MeCbm)$^5$,D-4Aph(MeCbm)$^6$]-Antide. Cleavage from the resin and deprotection, followed by purification, are carried out as described in Example 1. The peptide Ac-D-2Nal-D-4Cpa-D-3Pal-Ser-4Aph(methylcarbamoyl)-D-4Aph(methylcarbamoyl)-Leu-Lys(isopropyl)-Pro-D-Ala-NH$_2$ is obtained in the RP-HPLC purification. It is judged to be substantially homogeneous, and its purity is estimated to be greater than 99 percent. MS analysis shows a mass of 1562.8 Da, which is in agreement with the calculated mass of 1562.8 Da.

Assaying this peptide in the standard in vivo rat test as in Example 1, shows that, at a dosage of 50 micrograms, the peptide is bioactive and about as effective as Acyline for two days and then begins to drop off somewhat in its suppression of LH.

EXAMPLE 2

The peptide [4Aph(Hor)$^5$, D-Cit$^6$]-Antide, an analog of the peptide Cetrorelix having the formula Ac-D-2Nal-D-4Cpa-D-3Pal-Ser-4Aph(L-hydroorotyl)-D-cit-Leu-ILys-Pro-D-Ala-NH$_2$ is synthesized using the synthesis as generally set forth in Example 1. Instead of N$^\alpha$Boc-D-4Aph, N$^\alpha$Boc-D-Cit is coupled in the 6-position. Alternatively, N$^\alpha$Boc-D-Orn(Fmoc) is coupled in the 6-position, and the chain elongation is temporarily halted after having obtained the following peptide intermediate: Boc-D-Orn(Fmoc)-Leu-Lys(ipr,Z)-Pro-D-Ala-NH-[MBHA resin support]. The amino side chain on the Orn residue is then deprotected by removal of the Fmoc protection as in Example 1, and the intermediate is treated with excess t-butyl isocyanate in DMF about 6 hours at room temperature to react with the side chain of the Orn residue. The completion of the synthesis of the decapeptide intermediate is then carried out as in Example 1.

The peptidoresin is then washed, cleaved and deprotected, and then purified as described in Example 1. The peptide Ac-D-2Nal-D-4Cpa-D-3Pal-Ser-4Aph(L-hydroorotyl)-D-Cit-Leu-ILys-Pro-D-Ala-NH$_2$ is obtained in the RP-HPLC purification. It is judged to be substantially homogeneous, and its purity is estimated to be greater than 99 percent. LSIMS analysis shows measured mass of 1583.7 Da which is in agreement with the calculated mass of 1583.8 Da for this peptide.

The peptide is more hydrophilic than Cetrorelix and exhibits as long duration of bioactivity as Cetrorelix when tested in vivo for suppression of LH secretion as in Example 1. It has marginally better suppression at 3 days and substantially better at 96 hours.

EXAMPLE 2A

An analog of the peptide Antide, i.e. [4Aph(Hor)$^5$]-Antide is synthesized using the synthesis as generally set forth in Example 1 of U.S. Pat. No. 5,169,935. After coupling N$^\alpha$Boc-D-Lys(Fmoc) in the 6-position, it is reacted with an excess of nicotinic acid in DMF following deprotection. Then, N$^\alpha$Boc-Aph(Fmoc) is coupled in the 5-position, and the amino side chain on the Aph residue is then deprotected as in Example 1. The intermediate is reacted with L-hydroortic acid in DMF, and the synthesis of the decapeptide intermediate is completed as in Example 1.

Following the standard wash, cleavage from the resin, deprotection and purification are carried out as described in Example 1. The peptide Ac-D-2Nal-D-4Cpa-D-3Pal-Ser-4Aph(L-hydroorotyl)-D-Lys(Nic)-Leu-ILys-Pro-D-Ala-NH$_2$ is obtained in the RP-HPLC purification. It is considered to be more hydrophilic than Cetrorelix and to exhibit as long duration of bioactivity as Cetrorelix for suppression of LH secretion.

EXAMPLE 3

The analog [4Aph(D/L-Imz)$^5$]-Acyline is synthesized following the method generally set forth in Example 1B, except that D/L-Imz is substituted for L-Hor. Thus, following deprotection of 4Aph in the 5-position, the intermediate is treated with an excess of D/L-2-Imidazolidone-4-carboxylic acid, about 90 mg of HOBt and about 0.66 mmol of DIC in DMF solution for about 6 hours at room temperature. The completion of the synthesis of the decapeptide intermediate is then carried out as in Example 1.

The peptidoresin is washed, cleaved and deprotected and purified as described in Example 1. The peptide Ac-D-2Nal-D-4Cpa-D-3Pal-Ser-4Aph(D/L-2-imidazolidone-4-carbonyl)-D-4Aph(Ac)-Leu-ILys-Pro-D-Ala-NH$_2$ is obtained in the RP-HPLC purification. It is judged to be homogeneous mixture of two compounds, without other impurities. LSIMS analysis shows a measured mass of 1602.7 Da which is in agreement with the calculated mass of 1602.8 Da for this peptide.

Assaying the peptide using the standard in vivo rat test as in Example 1 shows that, at a dosage of 50 micrograms, the peptide exhibits long duration of suppression of LH secretion. It has marginally better suppression at 3 days and at 96 hours than Acyline.

EXAMPLE 3A

The synthesis of Example 3 is repeated using an excess of L-2-imidazolidone-4-carboxylic acid instead of D/L-Imz. The resultant peptide is judged to be substantially homogeneous and its purity is estimated to be about 99 percent. LSIMS analysis shows a measured mass of 1602.5 Da, which is in agreement with the calculated mass of 1602.8 Da for this peptide. The peptide is more water soluble than Acyline.

Assaying is carried out as in Example 1, and at a dosage of 50 micrograms, the peptide exhibits long duration of suppression of LH secretion, being about the same as Acyline over a period of 96 hours.

EXAMPLE 3B

The synthesis of Example 3 is repeated using an excess of D-2-imidazolidone-4-carboxylic acid instead of D/L-Imz. The resultant peptide Ac-D-2Nal-D-4Cpa-D-3Pal-Ser-4Aph (D-Imz)-D-4Aph(Ac)-Leu-ILys-Pro-D-Ala-NH$_2$ is obtained. LSIMS analysis shows a measured mass of 1602.6 Da, which is in agreement with the calculated mass of 1602.8 Da for this peptide. The peptide is more water soluble than Acyline.

Assaying is carried out as in Example 1. The peptide is bioactive and at a dosage of 50 micrograms, the peptide exhibits suppression of LH secretion.

EXAMPLE 3C

The peptide [4Aph(Imz)$^5$, D-4Amf(Cbm)$^6$]-Acyline is synthesized using a combination of the methods set forth in Examples 1A (to introduce D-4Amf(Cbm)$^6$) and 3A (to introduce 4Aph(Imz)$^5$). The peptide Ac-D-2Nal-D-4Cpa-D-3Pal-Ser-4Aph(L-Imz)-D-4Amf(carbamoyl)-Leu-ILys- Pro-D-Ala-NH$_2$ is obtained in the RP-HPLC purification. It is judged to be substantially homogeneous, and its purity is estimated to be greater than 98 percent. LSIMS analysis shows a measured mass of 1617.6 Da which is in agreement with the calculated mass of 1617.8 Da for this peptide. The peptide is assayed as in Example 1, and at a dosage of 50 micrograms, it exhibits a long duration of suppression of LH secretion. It is substantially the same as Acyline over 3 days and has a somewhat superior suppression at 96 hours.

EXAMPLE 4

The peptide [4Aph(Hor)$^5$, D-4Amf (MeCbm )$^6$]-Antide, having the formula Ac-D-2Nal-D-4Cpa-D-3Pal-Ser-4Aph (L-hydroorotyl)-D-4Amf(MeCbm)-Leu-Ilys-Pro-D-Ala-NH$_2$ is synthesized using the synthesis as generally set forth in Example 1A. Instead of reacting D-4Amf in the 6-position with excess t-butyl isocyanate in DMF, it is reacted with methyl isocyanate. The completion of the synthesis of the decapeptide intermediate is then carried out as in Example 1A.

The peptidoresin is washed, cleaved and deprotected, and purified, as described in Example 1. The peptide Ac-D-2Nal-D-4Cpa-D-3Pal-Ser-4Aph(L-hydroorotyl)-D-4Amf (MeCbm)-Leu-ILys-Pro-D-Ala-NH$_2$ is obtained in the RP-HPLC purification. It is judged to be substantially homogeneous, and its purity is estimated to be greater than 99 percent. LSIMS analysis shows measured mass of 1659.8 Da which is in agreement with the calculated mass of 1659.8 Da for this peptide.

Assaying the peptide using the standard in vivo rat test shows that, at a dosage of 50 micrograms, Peptide No. 4 exhibits better suppression of LH secretion than Acyline and is considered to exhibit very long-acting duration of bioactivity.

EXAMPLE 4A

The synthesis of Example 4 is repeated substituting acetic anhydride for methyl isocyanate to create the peptide [4Aph (Hor)$^5$, D-4Amf(Ac)$^6$]-Antide. The peptide Ac-D-2Nal-D-4Cpa-D-3Pal-ser-4Aph(L-hydroorotyl)-D-4Amf(Ac)-Leu-ILys-Pro-D-Ala-NH$_2$ is obtained in the RP-HPLC purification. It is judged to be substantially homogeneous, and its purity is estimated to be greater than 99 percent. LSIMS analysis shows a measured mass of 1644.5 Da which is in agreement with the calculated mass of 1644.8 Da for this peptide.

The peptide is assayed as in Example 1 at a dosage of 50 micrograms, and it exhibits long-acting duration of bioactivity. It shows suppression of LH secretion equal to Acyline for 3 days and at 96 hours is slightly superior to Acyline.

EXAMPLE 4B

A modification of the decapeptide synthesized and tested in Example 1A is made having D-alaninol at the C-terminus instead of D-alanylamide. A nonapeptide fragment is first synthesized having proline as a free acid at the C-terminus using a synthesis generally as described with respect to Example 1A, but using a Merrifield resin (chloromethylated cross-linked polystyrene) such as; that available from Bachem, Inc. Following cleavage, deprotection and purification, the following nonapeptide is obtained: Ac-D-2Nal-D-4Cpa-D-3Pal-Ser-4Aph(Hor)-D-4Amf(Cbm)-Leu-ILys-Pro-OH. 0.15 mmol of the completely deprotected and HPLC-purified nonapeptide is dissolved in 3 ml of dry DMF along with 3.0 mmol of D-alaninol (Lancaster Chemical). Then, 0.60 mmol of PyBOP (Novabiochem), a solid, was added as a coupling agent, and the reaction mixture was stirred at room temperature for 30 minutes. The reaction was quenched by adding 200 ml of water, creating an emulsion which was converted to a clear solution by adjusting the pH to 2.5 using glacial acetic acid. The resultant decapeptide, Ac-D-2Nal-D-4Cpa-D- 3Pal-Ser-4Aph(Hor)-D-4Amf (Cbm)-Leu-ILys-Pro-D-Ala-ol, was purified using preparative RP-HPLC using TEAP (pH 2.3) as a buffer, followed by a further purification using 0.1% TFA as a buffer. The resultant peptide is judged to be substantially homogeneous, and its purity is estimated to be greater than about 99%. MS analysis shows a mass of 1632.9 Da which is in agreement with the calculated mass of 1632.8 Da.

Assaying this peptide in the standard in vivo rat test, as in Example 1, shows that, at a dosage of 50 micrograms, the peptide is bioactive, and such bioactivity. continues for at least 96 hours. The peptide is considered to be very long-acting.

EXAMPLE 4C

The synthesis of Example 4B is repeated substituting 3.0 mmol of L-alaninol (Aldridge Chemical) for D-alaninol in the reaction mixture. The resultant decapeptide is purified as in Example 4B and is judged to be substantially homogeneous, having a purity estimated to be greater than about 98%. MS analysis shows a mass of 1632.9 Da which is in agreement with the calculated mass of 1632.8 Da.

Assaying this peptide in the standard in vivo rat test, as in Example 1, shows that, at a dosage of 50 micrograms, the peptide is bioactive, and such bioactivity continues for at least 96 hours. The peptide is considered to be very long-acting.

EXAMPLE 4D

A modification of the decapeptide synthesized and tested in Example 1 is made having D-alaninol at the C-terminus instead of D-alanylamide. A nonapeptide fragment is synthesized having proline as a free acid at the C-terminus using SPPS on a Merrifield resin, but otherwise generally as described with respect to Example 1. Following cleavage, deprotection and purification, the following nonapeptide is obtained: Ac-D-2Nal-D-4Cpa-D-3Pal-Ser-4Aph(Hor)-D-4Aph(Cbm)-Leu-ILys-Pro-OH. The purified nonapeptide is then reacted with D-alaninol as in Example 4B, and the resultant decapeptide, Ac-D-2Nal-D-4Cpa-D-3Pal-Ser-4Aph(Hor)-D-4Aph(Cbm)-Leu-ILys-Pro-D-Ala-ol, is purified using preparative RP-HPLC as described in Example 4B, with the exception of using TEAP at pH 6.5 instead of TEAP at pH 2.3. The resultant peptide is judged to be substantially homogeneous, having a purity estimated to be greater than about 99%. MS analysis shows a mass of 1618.9 Da which is in agreement with the calculated mass of 1618.8 Da. Assaying the peptide invivo shows it to be bioactive.

EXAMPLE 4E

The synthesis described in Example 4D is repeated, substituting L-alaninol for D-alaninol. The resultant decapeptide: Ac-D-2Nal-D-4Cpa-D-3Pal-Ser-4Aph(Hor)-D-4Aph(Cbm)-Leu-ILys-Pro-Ala-ol, is purified using preparative RP-HPLC as described in Example 4D, and the resultant peptide is judged to be substantially homogeneous, having a purity estimated to be greater than about 99%. MS analysis shows a mass of 1618.9 Da which is in agreement with the calculated mass of 1618.8 Da. Assaying the peptide in vivo shows it to be bioactive.

EXAMPLE 5

The peptide [4Aph(D-Hor)$^5$, D-4Amf(Cbm)$^6$]-Antide, one which has the formula Ac-D-2Nal-D-4Cpa-D-3Pal-Ser-4Aph(D-hydroorotyl)-D-4Amf(Cbm)-Leu-ILys-Pro-D-Ala-NH$_2$ is synthesized using the synthesis as generally set forth in Example 1A. Instead of reacting 4Aph in the 5-position with L-hydroorotic acid, the side chain is reacted with D-hydroorotic acid. The completion of the synthesis of the decapeptide intermediate is then carried out as in Example 1A.

The peptidoresin is then subjected to the standard wash, and cleavage from the resin and deprotection, followed by purification, are carried out as described in Example 1. The peptide Ac-D-2Nal-D-4Cpa-D-3Pal-Ser-4Aph(D-hydroorotyl)-D-4Amf (Cbm)-Leu-ILys-Pro-D-Ala-NH$_2$ is obtained in the RP-HPLC purification. It is judged to be substantially homogeneous, and its purity is estimated to be greater than 98 percent. LSIMS analysis shows measured mass of 1645.8 Da which is in agreement with the calculated mass of 1645.8 Da for this peptide.

Assaying the peptide using the standard in vivo rat test shows that, at a dosage of 50 micrograms, the peptide exhibits a duration of bioactivity in the suppression of LH secretion over 2 days about as long as Acyline and continues to effect some lesser degree of suppression at 72 and 96 hours.

EXAMPLE 5A

The synthesis of Example 5 is repeated except that, instead of reacting the deprotected side chain of 4Amf with t-butyl isocyanate, it is reacted with acetic anhydride. The peptide Ac-D-2Nal-D-4Cpa-D-3Pal-Ser-4Aph(D-hydroorotyl)-D-4Amf (Ac)-Leu-ILys-Pro-D-Ala-NH$_2$ is obtained in the RP-HPLC purification. It is judged to be substantially homogeneous, and its purity is estimated to be greater than 99 percent. LSIMS analysis shows a measured mass of 1644.7 Da which is in agreement with the calculated mass of 1644.8 Da for this peptide.

The peptide is assayed as in Example 1, and at a dosage of 50 micrograms, the peptide exhibits a suppression of LH secretion substantially the same as Acyline over 3 days; at 96 hours, it exhibits a suppression of LH somewhat superior to Acyline.

EXAMPLE 6

The synthesis as generally set forth in Example 1F is repeated with the exception that N$^\alpha$Boc-D-4Amf(Fmoc) is used for the 6-position residue instead of N$^\alpha$Boc-D-4Aph (Fmoc) to form the decapeptide [4Amf(Hor)$^5$, D-4Amf(Ac)$^6$]-Antide. The peptide Ac-D-2Nal-D-4Cpa-D-3Pal-Ser-4Amf(L-hydroorotyl)-D-4Amf (acetyl)-Leu-Lys (isopropyl)-Pro-D-Ala-NH$_2$ is obtained in the RP-HPLC purification. It is judged to be substantially homogeneous, and its purity is estimated to be greater than 99 percent. MS analysis shows a mass of 1658.7 Da, which is in agreement with the calculated mass of 1658.8 Da.

The peptide is assayed as in Example 1, and at a dosage of 50 micrograms, the peptide is found to have long-acting duration in the suppression of LH secretion. It is about the same as Acyline over the first two days and exhibits a biopotency nearly equal to that of Acyline over days 3 and 4.

EXAMPLE 6A

The synthesis of Example 6 is repeated, except that instead of reacting the deprotected side chain of D-4Amf with acetic anhydride, it is reacted with t-butyl isocyanate as in Example 1 to form the peptide [4Amf(Hor)5, D-4Amf (Cbm)$^6$]-Antide. The decapeptide Ac-D-2Nal-D-4Cpa-D-3Pal-Ser-4Amf(L-hydroorotyl)-D-4Aph(carbamoyl)-Leu-Lys(isopropyl)-Pro-D-Ala-NH$_2$ is obtained in the RP-HPLC purification. It is judged to be substantially homogeneous, and its purity is estimated to be about 99 percent. MS analysis shows a mass of 1659.6 Da, which is in agreement with the calculated mass of 1659.8 Da The peptide is assayed as in Example 1, and at a dosage of 50 micrograms, it is as active as Acyline in the suppression of LH secretion after 1 day and nearly as active after 2 days. It is somewhat less active after 3 days but exhibits about the same activity as Acyline after 4 days.

EXAMPLE 6B

The synthesis of Example 6A is repeated, except that the reaction is carried out with methyl isocyanate instead of t-butyl isocyanate to create the peptide [4Amf(Hor)$^5$, D-4Amf (MeCbm)$^6$]-Antide. The peptide Ac-D-2Nal-D-4Cpa-D-3Pal-Ser-4Amf(L-hydroorotyl)-D-4Aph (methylcarbamoyl)-Leu-Lys(isopropyl)-Pro-D-Ala-NH$_2$ is obtained in the RP--HPLC purification. It is judged to be substantially homogeneous, and its purity is estimated to be about 99 percent. MS analysis shows a mass of 1673.6 Da, which is in agreement with the calculated mass of 1673.8 Da.

The peptide is tested in the assay as set forth in Example 1, and at a dosage of 50 micrograms, the peptide is as active as Acyline in the suppression of LH secretion after 1 day and about as active after 2 days. At 3 and 4 days, it continues to effect a significantly lesser degree of suppression of LH secretion than Acyline.

EXAMPLE 6C

The synthesis of Example 6 is repeated, substituting D-hydroorotic acid for L-hydroorotic acid to form the peptide [4Amf(D-Hor)$^5$, D-4Amf(Ac)$^6$]-Antide. The peptide Ac-D-2Nal-D-4Cpa-D-3Pal-Ser-4Amf(D-hydroorotyl)-D-4Amf(acetyl)-Leu-Lys(isopropyl)-Pro-D-Ala-NH$_2$ is obtained in the RP-HPLC purification. It is judged to be substantially homogeneous, and its purity is estimated to be greater than 99 percent. MS analysis shows a mass of 1658.7 Da, which is in agreement with the calculated mass of 1658.8 l)a.

The peptide is assayed as in Example 1, and at a dosage of 50 micrograms, it is substantially as effective as Acyline for days 1 and 2. At day 3, it is substantially less effective than Acyline and continues to significantly drop in biopotency thereafter.

EXAMPLE 7

Using the procedures as generally set forth in Examples 1 to 5, the following GnRH antagonist peptides are also prepared:

[4Aph(Hor)$^5$,D-4Amf(Cbm)$^6$, Pro$^9$NHCH$_2$CH$_3$]-Antide
[4Aph(Hor)$^5$,D-4Aph(Cbm)$^6$, Pro$^9$NHCH$_2$CH$_3$]-Antide
[Acr-D-2Nal$^1$,4FD-Phe$^2$,4Aph(Hor$^5$)]-Acyline
[Bz-D-2Nal$^1$,4NO$_2$D-Phe$^2$,4Aph(Hor)$^5$,D-4Aph(Hor)$^6$]-Antide
[For-D-2Nal$^1$,4OCH$_3$D-Phe$^2$,4Amf(Hor)$^5$,D-4Aph(D-Hor)$^6$]-Antide
[Acr-D-2Nal$^1$,4BrD-PheZ$^2$,4Aph(Imz)$^5$,D-4Aph(Imz)$^6$]-Antide
[Pn-D-2Nal$^1$,4CH$_3$D-Phe$^2$,3Aph(D-Imz)$^5$,D-4Aph(D-Hor)$^6$]-Antide
[By-D-2Nal$^1$,3,4Cl$_2$D-Phe$^2$,4Aph(Hor)$^5$,D-4Aph(Hor)$^6$]-Antide
[Vl-D-2Nal$^1$,4NO$_2$D-Phe$^2$,4Aph(Hor)$^5$,D-3Aph(Cbm)$^6$]-Antide
[Vac-D-2Nal$^1$,C$^\alpha$Me4ClD-Phe$^2$,4Aph(Hor)$^5$,Gly$^{10}$]-Acyline
[Pn-D-2Nal$^1$,3Aph(Imz)$^5$,D-3Amf(D-Hor)$^6$-Agl$^{10}$]-Antide
[Acr-D-2Nal$^1$,4Aph(Hor)$^5$,Arg(Et$_2$)$^8$, D-Agl(Me)$^{10}$]-Acyline
[MeCbm-D-2Nal$^1$,4Aph(Hor)$^5$,Arq$^8$,Agl(Me)$^{10}$]-Acyline
[Cbm-D-2Nal$^1$,3Amf(Imz)$^5$,Ala$^{10}$]-Acyline
[EtCbm-D-2Nal$^1$,4Amf (Hor)$^5$,Pro$^9$NHCH$_2$CH$_3$]-Acyline
[Acr-D-2Nal$^1$,4Aph(Imz)$^5$,D-4Amf(Cbm)$^6$, Arg$^8$]-Antide
[Cbm-D-2Nal$^1$,4Aph(MeCbm)$^5$,D-4Amf(Mecbm)$^6$,Arg (Et$_2$)$^8$]-Antide
[4Ahp(Hor)$^5$,D-4Ahp(Imz)$^6$, D-Agl$^{10}$]-Antide
[Ac-D-1Nal$^1$,4Amf(Hor)$^5$,D-4Amf(D-Hor)$^6$,Arg$^8$]-Antide
[PrCbm-D-2Nal$^1$,4Amf(Imz)$^5$,D-4Ahp(EtCbm )$^6$, Pro$^9$NHCH$_2$CH$_3$]-Antide
[4Amf(Hor)$^5$,D-Lys(Nic)$^6$,AzaGly$^{10}$]-Antide
[4Amf(Hor)$^5$,D-Cit$^6$,Har(Et$_2$)$^8$]-Antide
[4Aph(Hor)$^5$,D-Lys(Nic)$^6$,D-Agl$^{10}$]-Antide
[4Aph(Hor)$^5$,D-Hci$^6$,Agl(Me)$^{10}$]-Antide
[4Aph(Hor)$^5$,D-3Pal$^6$ ,Har$^8$,Agl$^{10}$]-Antide
[4Aph(Hor)$^5$,D-4Aph(For)$^6$,D-Agl(Me)$^{10}$]-Antide
[4Aph(Hor)$^5$,D-4Aph(atz)$^6$,Har(Et$_2$)$^8$]-Antide
[4Aph(Hor)$^5$,D-4Aph(iprCbm)$^6$,D-Agl$^{10}$]-Antide
[For-D-1Nal$^1$,4Amf(Hor)$^5$,D-4Amf(atz)$^6$,Gly$^{10}$]-Antide
[4Aph(D-Hor)$^5$,D-4Aph(Cbm)$^6$Ala$^{10}$-ol]-Antide These peptides are biopotent in inhibiting the secretion of LH.

EXAMPLE 8

Using the procedures as generally set forth in Examples 1 to 5 and in U.S. Pat. No. 5,491,217, the following GnRH antagonist peptides are also prepared:

[N$^\alpha$Me4Aph(Hor)$^5$,D-4Aph(Cbm)$^6$]-Antide
[N$^\alpha$Me4Aph(Hor)$^5$,D-4Amf(Cbm)$^6$]-Antide
[N$^\alpha$Me4Aph(Hor)$^5$]-Acyline
[N$^\alpha$Me4Aph(D-Hor)$^5$]-Acyline
[D-4FPhe$^2$,N$^\alpha$Me4Aph(Hor)$^5$]-Acyline
[N$^\alpha$Me4Amf(Hor)$^5$]-Acyline
[N$^\alpha$Me4Aph(Hor$^5$),D-4Aph(Hor)$^6$]-Antide
[N$^\alpha$Me4Aph(Hor$^5$),D-4Aph(D-Hor)$^6$]-Antide
[MeCbm-D-2Nal$^1$, N$^\alpha$Me4Aph(Hor)$^5$]-Acyline

[N<sup>α</sup>Me4Aph(Hor)⁵,D-3Pal⁶]-Antide
[N<sup>α</sup>Me4Aph(Cbm)⁵,D-4Aph(Cbm)⁶]-Antide
[N<sup>α</sup>Me4Aph(MeCbm)⁵,D-4Aph(MeCbm)⁶]-Antide
[N<sup>α</sup>Me4Aph(Hor),D-4Amf(Cbm)⁶, Ala¹⁰-ol]-Antide
[N<sup>α</sup>Me4Aph(Hor),D-4Aph(Cbm)⁶, D-Ala¹⁰o-ol]-Antide
[N<sup>α</sup>Me4Aph(Hor),D-4Aph(Cbm)⁶, Ala¹⁰-ol]-Antide
[N<sup>α</sup>Me4Aph(Hor)⁵,D-Cit⁶]-Antide
[N<sup>α</sup>Me4Aph(Hor)⁵,D-Lys(Nic)⁶]-Antide
[N<sup>α</sup>Me4Aph(D/L-Imz)⁵]-Acyline
[N<sup>α</sup>Me4Aph(L-Imz)⁵]-Acyline
[N<sup>α</sup>Me4Aph(D-Imz)⁵]-Acyline
[N<sup>α</sup>Me4Aph(L-Imz)⁵,D-4Amf(Cbm)⁶]-Acyline
[N<sup>α</sup>Me4Aph(Hor)⁵, D-4Amf(MeCbm)⁶]-Antide
[N<sup>α</sup>Me4Aph(Hor)⁵, D-4Amf(Ac)⁶]-Antide
[N<sup>α</sup>Me4Aph(Hor)⁵, D-4Amf(Cbm)⁶, D-Ala¹⁰-ol]-Antide
[N<sup>α</sup>Me4Aph(D-Hor)⁵, D-4Amf(Cbm)⁶]-Antide
[N<sup>α</sup>Me4Aph(D-Hor)5, D-4Amf(Ac)⁶]-Antide
[N<sup>α</sup>Me4Amf(Hor)⁵, D-4Amf(Ac)⁶]-Antide
[N<sup>α</sup>Me4Amf(Hor)⁵, D-4Amf(Cbm)⁶]-Antide
[N<sup>α</sup>Me4Amf(Hor)⁵, D-4Amf(MeCbm)⁶]-Antide
[N<sup>α</sup>Me4Amf(D-Hor)⁵, D-4Amf(Ac)⁶]-Antide These peptides are biopotent in inhibiting the secretion of LH and have very good solubility in water at physiologic pH.

The foregoing compounds which were tested were shown to exhibit biological potency in the suppression of LH to an extent at least generally comparable to the corresponding GnRH antagonist peptide known as Antide, of which they are considered to be analogs. As a result of extensive testing in this area for over a decade, biopotency determined in this widely accepted test measuring the suppression of LH has been accepted as evidence as to such compounds' ability to suppress gonadotropin secretion and thus to exhibit useful antigonadal anti-ovulatory effects. Based upon superior solubility, resistance to itivivo gelling, long duration of bioactivity and other properties, these compounds are considered to be generally useful as antigonadal agents to suppress the secretion of gonadotropins and inhibit the release of steroids by the gonads, e.g. as anti-ovulatory agents.

The compounds of the invention are often administered in the form of pharmaceutically acceptable, nontoxic salts, such as acid addition salts, or of metal complexes; acetate and pamoate, the salt of pamoic acid, may be preferred. If the active ingredient is to be administered in tablet form, the tablet may contain a pharmaceutically-acceptable, nontoxic diluent which includes a binder, such as tragacanth, corn starch or gelatin; a disintegrating agent, such as alginic acid; and a lubricant, such as magnesium stearate. Intravenous administration in isotonic saline, phosphate buffer solutions or the like may be effected.

The pharmaceutical compositions will usually contain an effective amount of the peptide in conjunction with a conventional, pharmaceutically-acceptable carrier or diluent. Usually, the dosage will be from about 10 micrograms to about 2.5 milligrams of the peptide per kilogram of the body weight of the host when given intravenously. The nature of these compounds may permit effective oral administration; however, oral dosages might be higher. Overall, treatment of subjects with these peptides is generally carried out in the same manner as the clinical treatment using other antagonists of GnRH, using a suitable carrier in which the compound is soluble and administering a dosage sufficient to suppress LH and FSH levels in the patient.

It may also be desirable to deliver the GnRH analog over prolonged periods of time, for example, for periods of one week to one year from a single administration, and slow release, depot or implant dosage forms may be utilized.

These compounds can be administered to mammals intravenously, subcutaneously, intramuscularly, orally, percutaneously, intranasally, intrapulmonarily, intrarectally or intravaginally to achieve fertility inhibition and/or control and also in applications calling for reversible suppression of gonadal activity, such as for the management of precocious puberty or during radiation- or chemotherapy. They are also useful for treatment of steroid-dependent tumors. Effective dosages will vary with the form of administration and the particular species of mammal being treated. Some of these compounds have solubilities as high as 50 mg/ml, and they commonly may be used as 5–10 mg/ml solutions at pH 5.4. An example of one typical dosage form is a bacteriostatic water solution at a pH of about 6 containing the peptide, which solution is administered parenterally to provide a dose in the range of about 0.1 to 2.5 mg/kg of body weight per day. These compounds are considered to be well-tolerated in vivo and to resist gelling; accordingly, they are considered to be particularly well-suited for administration by subcutaneous injection in a bacteriostatic water solution of about 5% mannitol at a pH of about 4.9, at appropriate concentrations, above about 0.75 mg/ml and even above about 1.0 mg/ml, without danger of gelling at the point of injection.

These GnRH antagonist peptides are also useful diagnostically, both invivo and in vitro. These peptides can be injected in vivo followed by assaying the bloodstream of a patient to determine the extent of decrease of hormonal secretion, e.g. LH secretion. In vitro assays can be carried out to determine whether certain tumor cells are sensitive to GnRH. In such assays, tumor cell cultures are treated with the GnRH antagonist peptides and then monitored for hormonal secretions and cell proliferation.

Although the invention has been described with regard to its preferred embodiments, it should be understood that changes and modifications as would be obvious to one having the ordinary skill in this art may be made without departing from the scope of the invention which is set forth in the claims which are appended hereto. Whereas the N-terminus may be left unsubstituted or other equivalent acylating groups can be used, either acetyl or substituted or unsubstituted carbamoyl is preferred. Instead of Aph or D-Aph, Ahp or D-Ahp can be used in the 5- and 6-position, respectively. Instead of Aph(Ac), the aminophe group can be treated with alternative acylating agents as disclosed in U.S. Pat. No. 5,506,207, such as formic acid, β-Ala(atz) and gamma-aminobutyric acid(atz), which likewise result in GnRH antagonists that exhibit long-acting duration; thus, the resulting residues are considered equivalents of D- and L-4Aph(Ac). Both Lys(Bu) and Lys(Et₂) are considered to be equivalents of ILys; however, ILys is most preferred. Other hydrophobic amino acid residues can also be employed in the 1-position and in the 6-position (as mentioned hereinbefore), preferably in D-isomer form, and are considered equivalents of those specified.

What is claimed is:

1. A GnRH antagonist peptide having the formula:

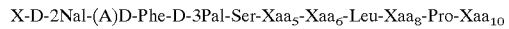

X-D-2Nal-(A)D-Phe-D-3Pal-Ser-Xaa₅-Xaa₆-Leu-Xaa₈-Pro-Xaa₁₀ or a pharmaceutically acceptable salt thereof wherein:

X is an acyl group having not more than 7 carbon atoms or Q, with Q being

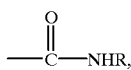

and with R being H or lower alkyl;
A is 4Cl, 4F, 4Br, 4NO$_2$, 4CH$_3$, 4OCH$_3$, 3,4Cl$_2$ or C$^\alpha$Me4Cl;
Xaa$_5$ is 4Aph(Q$_1$) or 4Amf(Q$_1$) with Q$_1$ being

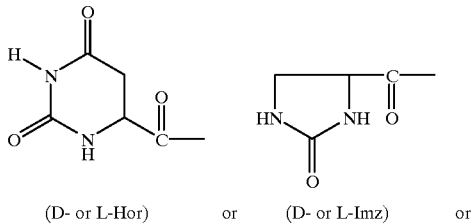

(D- or L-Hor)     or     (D- or L-Imz)     or a D/L mixture of either,
Xaa$_6$ is D-4Aph(Q$_2$), D-4Amf(Q$_2$), D-Lys(Nic), D-Cit, D-Hci or D-3Pal, with Q$_2$ being For, Ac, 3-amino-1,2,4-triazole(atz), Q or Q$_1$;
Xaa$_8$ is Lys(ipr), Arg, Har, Arg(Et$_2$) or Har(Et$_2$); and
Xaa$_{10}$ is D-Ala-ol or Ala-ol; provided however that the α-amino group of Xaa$_5$ may optionally be methylated; and provided further that when Xaa$_6$ contains D- or L-Hor or D- or L-Imz or a D/L mixture of either, Xaa$_5$ may have Ac, For or 3-amino-1,2,4-triazole as Q$_1$.

2. A GnRH antagonist peptide according to claim 1 wherein Q is carbamoyl or methylcarbamoyl.

3. A GnRH antagonist according to claim 1 wherein Q$_1$ is L-Hor or D-Hor.

4. A GnRH antagonist according to claim 1 wherein X is Ac and Xaa$_8$ is Lys(ipr).

5. A GnRH antagonist according to claim 1 wherein Xaa$_5$ is 4Aph(L- or D-Hor) and Xaa$_6$ is D-4Aph(Ac), D-4Aph(atz), or D-3Pal.

6. A GnRH antagonist according to claim 1 wherein Xaa$_5$ is 4Aph(L- or D-Hor), Q$_2$ is Q and R is H or methyl.

7. A GnRH antagonist according to claim 1 wherein Xaa$^5$ is 4Aph(L- or D-Hor) and Xaa$_6$ is D-Cit or D-Hci.

8. A GnRH antagonist according to claim 1 wherein Xaa$_6$ is D-4Aph(D-Hor).

9. A GnRH antagonist peptide according to claim 1 wherein:
X is For, Ac, Acr, Pn, By, Vl, Vac, Bz or Q;
A is 4Cl or 4F;
Xaa$_5$ is 4Aph(Q$_1$) or 4Amf(Q$_1$) with Q$_1$ being a D-isomer, an L-isomer, or a D/L-isomer mixture of either Hor or Imz;
Xaa$_6$ is D-4Aph(Q$_2$), D-4Amf(Q$_2$), D-Cit, D-Lys(Nic) or D-3Pal, with Q$_2$ being For, Ac, Q or Q$_1$; and
Xaa$_8$ is Lys(ipr).

10. A GnRH antagonist according to claim 9 wherein Q$_1$ is L- or D-Hor and Xaa$_6$ is D-4Amf(Q), with R being H or methyl.

11. A GnRH antagonist according to claim 9 wherein X is Ac or Q; R is H or methyl; Xaa$_6$ is D-4Aph(Q$_2$), D-4Amf(Q$_2$) or D-3Pal, with Q$_2$ being Ac, Q or Q$_1$.

12. A GnRH antagonist according to claim 1 having the formula: Ac-D-2Nal-D-4Cpa-D-3Pal-Ser-4Aph(L-Hor)-Xaa$_6$-Leu-Lys(ipr)-Pro-Xaa$_{10}$, wherein Xaa$_6$ is D-4Aph(Ac), D-3Pal, D-4Aph(carbamoyl), D-4Amf(carbamoyl), D-4Amf(methylcarbamoyl) or D-4Aph(D-Hor).

13. A pharmaceutical composition for inhibiting the secretion of gonadotropins in mammals comprising, as an active ingredient, an effective amount of a GnRH antagonist according to claim 12 in association with a nontoxic diluent.

14. A method for inhibiting the secretion of gonadotropins in mammals comprising administering an amount of a pharmaceutical composition according to claim 13 which effects a substantial decrease in LH and FSH levels.

15. A method for in vivo or in vitro diagnosis of a condition where GnRH is causing excess hormonal secretion or tumor growth, which method comprises administering a GnRH antagonist peptide according to claim 12 and monitoring for hormonal secretion or for tumor cell proliferation.

16. A GnRH antagonist according to claim 1 having either the formula: Ac-D-2Nal-D-4Cpa-D-3Pal-Ser-4Aph(L-Hor)-D-4Aph(carbamoyl)-Leu-Lys(ipr)-Pro-D-Ala-ol; or the formula Ac-D-2Nal-D-4Cpa-D-3Pal-Ser-4Aph(L-Hor)-D-4Aph(carbamoyl)-Leu-Lys(ipr)-Pro-Ala-ol.

17. A GnRH antagonist according to claim 1 having either the formula: Ac-D-2Nal-D-4Cpa-D-3Pal-Ser-4Aph(L-Hor)-D-4Amf(carbamoyl)-Leu-Lys(ipr)-Pro-D-Ala-ol; or the formula: Ac-D-2Nal-D-4Cpa-D-3Pal-Ser-4Aph(L-Hor)-D-4Amf(carbamoyl)-Leu-Lys(ipr)-Pro-Ala-ol.

18. A GnRH antagonist peptide having the formula:

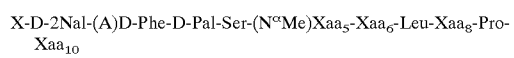

or a pharmaceutically acceptable salt thereof wherein:
X is an acyl group having not more than 7 carbon atoms or Q,
with Q being

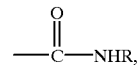

and with R being H or lower alkyl;
A is 4Cl, 4F, 4Br, 4NO$_2$, 4CH$_3$, 4OCH$_3$, 3,4Cl$_2$ or C$^\alpha$Me4Cl;
Xaa$_5$ is 4Aph(Q$_1$) or 4Amf(Q$_1$) with Q$_1$ being

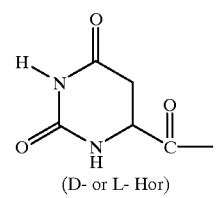

(D- or L- Hor)     or     (D- or L- Imz)

or a D/L mixture of either,
Xaa$_6$ is D-4Aph(Q$_2$), D-4Amf(Q$_2$), D-Lys(Nic), D-Cit, D-Hci or D-Pal, with Q$_2$ being For, Ac, 3-amino-1,2,4-triazole, Q or Q$_1$;
Xaa$_8$ is Lys(ipr), Arg, Har, Arg(Et$_2$) or Har(Et$_2$); and
Xaa$_{10}$ is D-Ala-NH$_2$, D-Ala-ol, Ala-ol, NHCH$_2$CH$_3$, Gly-NH$_2$, Ala-NH$_2$, AzaGly-NH$_2$, Agl-NH$_2$, D-Agl-NH$_2$, Agl(Me)-NH$_2$ or D-Agl(Me)-NH$_2$, provided however that when Xaa$_6$ contains D- or L-Hor or D- or L-Imz or a D/L mixture of either, Xaa$_5$ may have Ac, For or 3-amino-1,2,4-triazole as Q$_1$.

19. A GnRH antagonist peptide according to claim 18 wherein

Q is carbamoyl or methylcarbamoyl;

$Q_1$ is L-Hor or D-Hor; and $Xaa_{10}$ is D-Ala-NH$_2$, D-Ala-ol or Ala-ol.

20. A GnRH antagonist peptide according to claim 18 wherein:

X is For, Ac, Acr, Pn, By, Vl, Vac, Bz or Q;

A is 4Cl or 4F;

$Xaa_5$ is Aph($Q_1$) or Amf($Q_1$) with $Q_1$ being a D-isomer, an L-isomer, or a D/L-isomer mixture of either Hor or Imz;

$Xaa_6$ is D-Aph($Q_2$), D-Amf($Q_2$), D-Cit, D-Lys(Nic) or D-Pal, with $Q_2$ being For, Ac, Q or $Q_1$; and $Xaa_8$ is Lys(ipr).

\* \* \* \* \*

UNITED STATES PATENT AND TRADEMARK OFFICE
Certificate

Patent No. 6,214,798 B1                      Patented: April 10, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Graeme Semple, Gothenburg, Sweden; Guangcheng Jiang, San Diego, CA; and Jean E. F. Rivier, La Jolla, CA.

Signed and Sealed this Fourteenth Day of September 2004.

SREENI PADMANABHAN
*Supervisory Patent Examiner*
Art Unit 1617